United States Patent
Haddox et al.

(10) Patent No.: US 6,762,166 B2
(45) Date of Patent: *Jul. 13, 2004

(54) SYNTHETIC COMPLEMENTARY PEPTIDES AND OPHTHALMOLOGIC USES THEREOF

(75) Inventors: Jeffrey Lynn Haddox, Birmingham, AL (US); Roswell Robert Pfister, Harpersville, AL (US); James Edwin Blalock, Vestavia Hills, AL (US); Matteo Villain, Gorla Minore (IT)

(73) Assignee: Fornix Biosciences N.V., Lelystad (NL)

( * ) Notice: Subject to any disclaimer, the term of this patent is extended or adjusted under 35 U.S.C. 154(b) by 292 days.

This patent is subject to a terminal disclaimer.

(21) Appl. No.: 09/967,003

(22) Filed: Sep. 28, 2001

(65) Prior Publication Data

US 2002/0107202 A1 Aug. 8, 2002

Related U.S. Application Data

(63) Continuation of application No. 09/521,365, filed on Mar. 8, 2000, now Pat. No. 6,310,041.
(60) Provisional application No. 60/123,409, filed on Mar. 9, 1999.

(51) Int. Cl.[7] .................................. A61K 38/00
(52) U.S. Cl. .................. 514/12; 514/17; 514/18; 530/300; 530/324; 530/330; 530/331; 424/185.1
(58) Field of Search .................. 514/12, 17, 18; 530/300, 324, 330, 331; 424/185.1

(56) References Cited

U.S. PATENT DOCUMENTS 5,916,872 A * 6/1999 Chang .................. 514/9
6,310,041 B1 * 10/2001 Haddox .................. 514/12

FOREIGN PATENT DOCUMENTS

| WO | WO 00/53621 | 9/2000 |
| WO | WO 00/59931 | 10/2000 |

* cited by examiner

Primary Examiner—Christopher Tate
Assistant Examiner—Roy Teller
(74) Attorney, Agent, or Firm—Amster, Rothstein & Ebenstein LLP

(57) ABSTRACT

The present invention is directed to a series of complementary peptides for the pro-gly-pro sequence as antagonists of polymorphonuclear leukocyte chemoattractants. Also provided are applications of such peptides for treating alkali-injuried eyes and other types of diseases.

2 Claims, 1 Drawing Sheet

RTR tetramer
(MWt 2583.97 Da)

RTR dimer
(MWt 1272.45 Da)

ASA Tetramer
(MWt 1849.99 Da)

RTR monomer
(MWt 430.51 Da)

RTRGG monomer
(MWt 430.51 Da)

FIG. 1

SEQUENCE LISTING

```
<160> NUMBER OF SEQ ID NOS: 4

<210> SEQ ID NO 1
<211> LENGTH: 3
<212> TYPE: PRT
<213> ORGANISM: unknown organism
<220> FEATURE:
<223> OTHER INFORMATION: unknown organism: amino acid sequence of
      neutrophilic chemoattractant released during direct alkaline
      hydrolysis of corneal proteins; triggers polymorphonuclear
      leukocyte invasion into alkali-injured cornea

<400> SEQUENCE: 1

Pro Gly Pro
1

<210> SEQ ID NO 2
<211> LENGTH: 3
<212> TYPE: PRT
<213> ORGANISM: artificial sequence
<220> FEATURE:
<223> OTHER INFORMATION: description of artificial sequence: amino acid
      sequence of complementary peptide inhibitor of
      neutrophils; used as a monomer, dimer, and tetramer

<400> SEQUENCE: 2

Arg Thr Arg
1

<210> SEQ ID NO 3
<211> LENGTH: 5
<212> TYPE: PRT
<213> ORGANISM: artificial sequence
<220> FEATURE:
<223> OTHER INFORMATION: description of artificial sequence: amino acid
      sequence of complementary peptide inhibitor of
      neutrophils; used as a monomer
```

```
<400> SEQUENCE: 3

Arg Thr Arg Gly Gly
1               5

<210> SEQ ID NO 4
<211> LENGTH: 3
<212> TYPE: PRT
<213> ORGANISM: artificial sequence
<220> FEATURE:
<223> OTHER INFORMATION: description of artificial sequence: amino acid
      sequence of complementary peptide inhibitor of
      neutrophils; used as a tetramer

<400> SEQUENCE: 4

Ala Ser Ala
1
```

SYNTHETIC COMPLEMENTARY PEPTIDES AND OPHTHALMOLOGIC USES THEREOF

CROSS-REFERENCE TO RELATED APPLICATION

This patent application is a continuation of U.S. application Ser. No. 09/521,365, filed Mar. 8, 2000, and entitled "SYNTHETIC COMPLEMENTARY PEPTIDES AND OPHTHALMOLOGIC USES THEREOF", now U.S. Pat. No. 6,310,041 B1, issued Oct. 30, 2001, the contents of which are incorporated herein by reference in their entirety, which claims benefit of provisional patent application U.S. Serial No. 60/123,409, filed Mar. 9, 1999.

FEDERAL FUNDING LEGEND

This invention was produced in part using funds obtained through a grant from the National Institutes of Health (MH52527) and National Eye Institute EY04716. Consequently, the federal government has certain rights in this invention.

BACKGROUND OF THE INVENTION

1. Field of the Invention

The present invention relates generally to the biochemical pharmacology of ophthalmologic agents. More specifically, the present invention relates to synthetic complementary peptides and ophthalmologic uses thereof.

2. Description of the Related Art

Alkali-injury of the eye provokes an acute inflammatory reaction, largely composed of polymorphonuclear leukocytes (PMNs), which are responsible for corneal ulcerations and perforations.[1-3] N-acetyl-PGP and N-methyl-PGP, neutrophilic chemoattractants released during direct alkaline hydrolysis of corneal proteins, are the initial triggers for polymorphonuclear leukocyte invasion into the alkali-injured cornea.[4-6] The specific activity of N-acetyl-PGP is greater than the methylated tripeptide.[4]

Recognition that N-acetyl-PGP is an important mediator in this disease has opened a therapeutic window of opportunity. Early inhibition of this chemoattractant in an alkali-injured eye might reduce or eliminate the first neutrophilic influx. Minimizing the number of neutrophils initially penetrating into the damaged cornea would limit the production of secondary inflammatory mediators, such as leukotriene $B_4$, hence reducing the additional recruitment of polymorphonuclear leukocytes. Exclusion of neutrophils from the alkali-injured cornea is the key to decreasing or eliminating corneal ulceration. It is therefore of paramount importance to search for lead compounds which can inhibit this chemoattractant.

One approach to the development of a lead inhibitory compound can be found in the molecular recognition theory.[7] This concept posits that a fundamental requirement for biological reactions is that proteinaceous molecules recognize one another in a genetically defined manner. Blalock and Smith[8] proposed a novel approach to molecular recognition which has succeeded in predicting the interactions of proteinaceous molecules with high frequency. This method, based on the development of complementary peptides specified by ligand antisense RNA, has proven useful in designing interactive peptides, isolating receptors, and producing anti-receptor and anti-idiotypic antibodies.[9,10]

Thus, the prior art is deficient in synthetic complementary peptides to treat ophthalmologic disorders. The present invention fulfills this long-standing need and desire in the art.

SUMMARY OF THE INVENTION

The present invention demonstrates an application of the molecular recognition theory, which is the generation of therapeutic agents that may be used to treat disease. Using this approach, a series of complementary peptides for the pro-gly-pro (SEQ ID NO:1) sequence were designed, synthesized, and tested as antagonists of the PMN chemoattractant, N-acetyl-PGP.

In an embodiment of the present invention, there is provided a pharmaceutical composition for ophthalmologic uses. Specifically, such composition is a complementary peptide which comprises complementary sequences to proline-glycine-proline (PGP). Generally, the complementary sequences are designed based on the possible coding triplet for proline and glycine and on the hydropathic value of the two amino acids. Enhancement of the potency of the complementary sequence was achieved with a multimerization process. The resulting molecule can be divided into 4 specific subunits, connected by amide bonds with different functions: 1) recognition subunit 2) core multimerizing subunit 3) spacer subunit and 4) R N-terminal subunit.

The recognition subunit: the complementary sequence to Pro-Gly-Pro, this subunit is responsible for the interaction with the chemoattractant. The recognition subunit is present as a single unit in the monomer, is repeated twice in the dimer, 4 times in the tetramer and 8 times in the octamer. It is defined by the sequence all-L Arg-Thr-Arg and by the sequence all-L Xxx-Thr-Arg (Xxx=the 20 natural amino acids), and by all-D Arg-Thr-Arg and all-D Xxx-Thr-Arg (Xxx=the 20 natural amino acids).

The core multimerizing subunit, absent from the linear monomers, is characterized by a branching di-amino amino acid (lysine, di-amino propionic acid, di-amino butyric acid) connected to a single alanine, where both amino groups are involved in an amide bond. The function of the core is to determine the number of recognition units in the molecule and to control the relative spatial distribution of the recognition subunits. The core also represents the connection point to the resin during Solid Phase Peptide Synthesis. The octameric core is defined by the formula all-L $(((B)_2B)_2)$B-Ala, the tetramer by all-L $(B)_2$B-Ala and the dimer by all-L B-Ala (where B=lysine, di-amino propionic acid and di-amino butyric acid). The core was also obtained with all-D amino acids with the same generic formulas.

The spacers represent the connection point between the core and the recognition subunits and determines the relative spatial distribution of the recognition subunits. It can be constituted by a di-glycine. The di-glycine could be substituted by a single amino acid with the formula: $NH_2[CH_2]_n$—COOH [n=2[3-amino propionic acid];3;4;5;6; or 7[8-amino caprylic acid]]

R-terminal subunit: A free amino terminal group on each recognition subunit is not necessary for the subunit function. This group can be functionalized by an R molecule to modify the pharmaco-dynamic properties of the molecule and to produce a more constrained molecule. The R can be $H_3C$—$(CH_2)_n$—CO with n=0 (acetyl), n=4 (caproyl) and n=14 (palmitoleyl). R can also be the amino acid cysteine. In the case of the tetrameric peptide the sulfur groups could be used for the formation of an intra molecular di-sulfide bridge, generating a constrained bi-cyclic molecule.

In another embodiment of the present invention, there is provided a method of inhibiting polymorphonuclear leukocyte polarization, chemotaxis and infiltration into tissue activated by a neutrophil chemoattractant in an individual by administering the pharmaceutical composition of the present invention to the individual. Preferably, the neutrophil chemoattractant is selected from the group consisting of N-acetyl-PGP, N-acetyl-PGX, N-methyl-PGX, N-methyl-PGP and small peptide chemoattractants containing proline and glycine. Still preferably, the pharmaceutical composition is administered at a concentration range of from about 1 µM to about 100 mM, depending on the peptide.

In still another embodiment of the present invention, there is provided a method of treating an eye disease in a n individual by administering the claimed pharmaceutical composition. Preferably, the pharmaceutical composition is administered at a concentration range of from about 1 µM to about 100 mM, depending on the peptide. Representative eye diseases which can be treated using this method of the present invention include alkali-injured eye, chemically injured eye or inflammatory diseases of the eye which are well known to those having ordinary skill in this art.

Other and further aspects, features, and advantages of the present invention will be apparent from the following description of the presently preferred embodiments of the invention. These embodiments are given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

DETAILED DESCRIPTION OF THE INVENTION

The neutrophil chemoattractant, -acetyl-PGP, plays a major role in the initiation of polymorphonuclear leukocyte (PMN) invasion into the alkali-injured eye. In the current study, sense-antisense methodology was used to develop complementary peptides as potential inhibitors of N-acetyl-PGP. The polarization assay was used to measure the potential chemotactic response of polymorphonuclear leukocytes to synthetic N-acetyl-PGP, the ultrafiltered tripeptide chemoattractants obtained from alkali-degraded rabbit corneas, or leukotriene $B_4$. Inhibition was expressed as the peptide concentration required to produce 50% inhibition ($ID_{50}$) of polarization. Five complementary peptides were tested as potential inhibitors of N-acetyl-PGP: RTR (SEQ ID NO:2), RTRGG (SEQ ID NO:3), RTR dimer, RTR tetramer, and ASA (SEQ ID NO:4) tetramer. In addition, the RTR tetramer and both monomeric peptides (RTR and RTRGG) were tested, separately, for inhibition of the ultrafiltered tripeptide chemoattractants or $LTB_4$.

The complementary RTR tetrameric peptide was a powerful antagonist of N-acetyl-PGP induced polymorphonuclear leukocyte polarization ($ID_{50}$ of 200 nM). The RTR dimer was much less potent ($ID_{50}$ of 105 µM). Both monomeric peptides, RTR and RTRGG, were only antagonistic at millimolar concentrations. The ASA tetramer showed no capacity to inhibit N-acetyl-PGP. The RTR tetramer also inhibited polymorphonuclear leukocyte activation b y the ultrafiltered tripeptide chemoattractants ($ID_{50}$ of 30 µM), but had no effect on $LTB_4$. A complementary peptide (RTR) was designed which is an effective inhibitor of the neutrophil chemoattractant, N-acetyl-PGP. The peptide's potency is dramatically enhanced by tetramerization. Inhibition of this chemoattractant in the alkali-injured eye by complementary peptides offers great promise for control of the inflammatory response attendant to such injuries.

In one embodiment, the present invention is directed to a pharmaceutical composition for ophthalmologic uses. Specifically, this composition is a complementary peptide which comprises complementary sequences to proline-glycine-proline (PGP). Generally, the complementary sequences are designed based on the possible coding triplet for proline and glycine and on the hydropathic value of the two amino acids. Enhancement of the potency of the complementary sequence was achieved with a multimerization process. The resulting molecule can be divided into 4 specific subunits, connected by amide bonds with different functions: 1) recognition subunit 2) core multimerizing subunit 3) spacer subunit and 4) R N-terminal subunit.

Recognition subunit: the complementary sequence to Pro-Gly-Pro, this subunit is responsible for the interaction with the chemoattractant. It is present as a single unit in the monomer, is repeated twice in the dimer, 4 times in the tetramer and 8 times in the octamer. The recognition subunit is defined by the sequence all-L Arg-Thr-Arg and by the sequence all-L Xxx-Thr-Arg (Xxx=the 20 natural amino acids), and by all-D Arg-Thr-Arg and all-D Xxx-Thr-Arg (Xxx=the 20 natural amino acids).

The core multimerizing subunit, absent from the linear monomers, is characterized by a branching di-amino amino acid (lysine, di-amino propionic acid, di-amino butyric acid) connected to a single alanine, where both amino groups are involved in an amide bond. The function of the core is to determine the number of recognition units in the molecule and to control the relative spatial distribution of the recognition subunits. The core also represents the connection point to the resin during Solid Phase Peptide Synthesis. The octameric core is defined by the formula all-L $(((B)_2B)_2)B$-Ala, the tetramer by all-L $(B)_2B$-Ala and the dimer by all-L B-Ala (where B=lysine, di-amino propionic acid and di-amino butyric acid). The core was also obtained with all-D amino acids with the same generic formulas.

The spacers represent the connection point between the core and the recognition subunits and determines the relative spatial distribution of the recognition subunits. It can be constituted by a di-glycine. The di-glycine could be substituted by a single amino acid with the formula: $NH_2[CH_2]_n$—COOH [n=2[3-amino propionic acid];3;4;5;6; or 7[8-amino caprylic acid]].

R-terminal subunit: A free amino terminal group on each recognition subunit is not necessary for the subunit function. This group can be functionalized by an R molecule to modify the pharmaco-dynamic properties of the molecule and to produce a more constrained molecule. The R can be $H_3C$—$(CH_2)_n$—CO with n=0 (acetyl), n=4 (caproyl) and n=14 (palmitoleyl). R can also be the amino acid cysteine. In the case of the tetrameric peptide the sulfur groups could be used for the formation of an intra molecular di-sulfide bridge, generating a constrained bi-cyclic molecule.

In another embodiment of the present invention, there is provided a method of inhibiting polymorphonuclear leukocyte polarization, chemotaxis and infiltration into tissue activated by a neutrophil chemoattractant in an individual by administering the pharmaceutical composition of the present invention to the individual. Representative neutrophil chemoattractants include N-acetyl-PGP, N-acetyl-PGX, N-methyl-PGX, N-methyl-PGP and small peptide chemoattractants containing proline and glycine. Still preferably, the pharmaceutical composition is administered at a concentration range of from about 1 µM to about 100 mM, depending on the peptide.

In still another embodiment of the present invention, there is provided a method of treating an eye disease in a n individual by administering the claimed pharmaceutical composition. Preferably, the pharmaceutical composition is administered at a concentration range of from about 1 µM to about 100 mM, depending on the peptide. Still preferably, the eye disease can be alkali-injured eye, chemically injured eye or inflammatory disease of the eye.

As used herein, the term "multimer" shall refer to a dimer, tetramer or octamer.

The following examples are given for the purpose of illustrating various embodiments of the invention and are not meant to limit the present invention in any fashion:

EXAMPLE 1
Materials

Hanks balanced salt solution (HBSS) was purchased from Gibco Laboratories (Chagrin Falls, Ohio). Calcium chloride, magnesium chloride, sodium chloride, sodium phosphate monobasic and sodium phosphate dibasic, glutaraldehyde, and Ficoll (Type 400) were obtained from Sigma Chemical Co (St Louis, Mo.). Hypaque-76 was acquired from Winthrope Laboratories (New York, N.Y.). Leukotriene $B_4$ ($LTB_4$) was purchased from Biomol Research Laboratories (Plymouth Meeting, Pa.). Amino acids and resins used in the synthesis of peptides were from Perseptive Biosystem (Framingham, Mass.). N,N-Dimethylformamide, methylene chloride and other solvents used in the synthesis were from Fisher Scientific (Fair Lawn, N.J.).

EXAMPLE 2
Complementary Peptide Design

The complementary sequences to PGP were designed based on the possible coding triplet for proline and glycine and on the hydropathic value of these two amino acids. Glycine is a slightly hydrophilic amino acid and normally complemented by serine or threonine. The hydropathic characteristics of proline are not well defined. In the Kyte and Doolittle scale[11], proline is considered a slightly hydrophilic amino acid, however the structural characteristic of the side chain of proline should impart a more hydrophobic character. This is reflected in the Akamatsu and Fujita scale[12], where the hydrophobic value is close to other hydrophobic amino acids, exactly between alanine and methionine.

Figure 1:
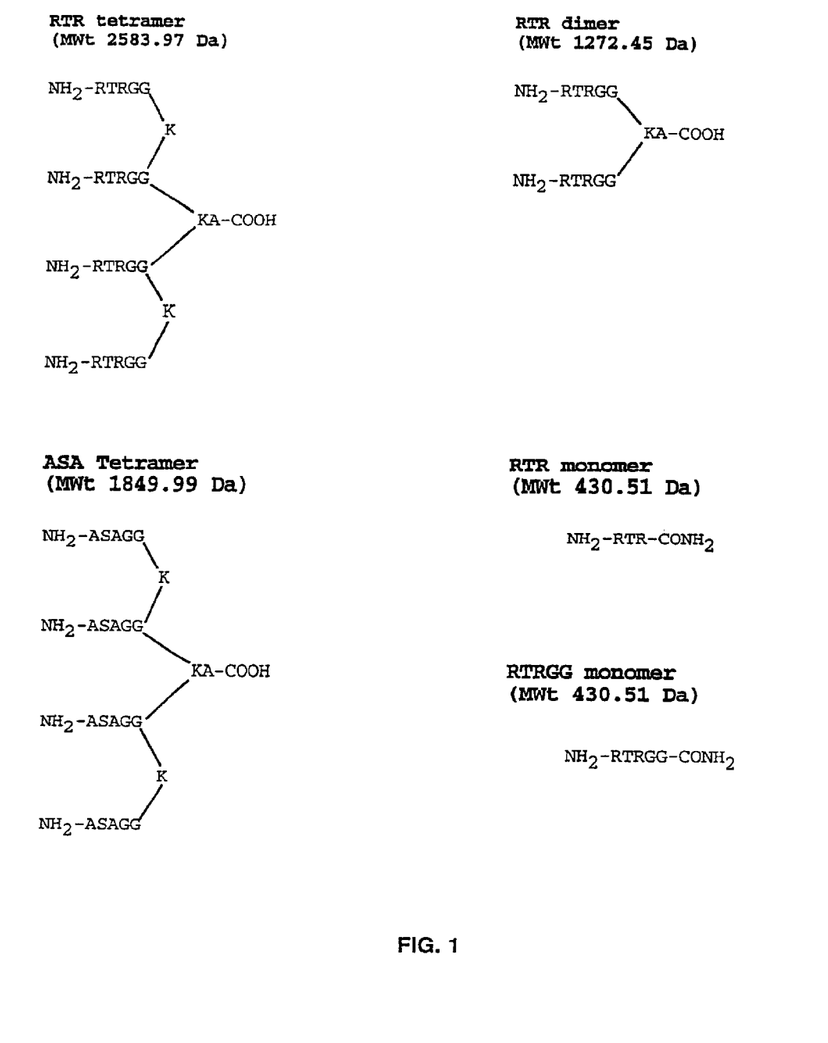
FIG. 1 shows the multimeric structure and molecular weights of antisense peptides which have been tested.

Two different complementary peptides, reflective of these two possible hydropathic characteristics of proline, were synthesized. A slightly hydrophilic proline is best complemented b y alanine, so the sequence ASA was chosen. A hydrophobic proline is best genetically complemented by arginine, and RTR was chosen. To increase the potential affinity for N-acetyl-PGP, complementary peptides were synthesized in multimeric forms, starting from a polylysine core, and spaced from the core with two glycines. The simple linear RTR and RTRGG sequences were also synthesized to verify the specificity of the RTR sequence in the multimeric peptides (FIG. 1).

EXAMPLE 3
Peptide Synthesis and Isolation

Complementary peptides were synthesized using Solid Phase Peptide synthesis following Fmoc methodology on a 9050 Peptide synthesizer from Perseptive Biosystem. The linear peptides were synthesized using an Amide-polyethylene glycol graft polystyrene (PEG-PS) resin and O-pentafluorophenyl ester pre-activated amino acids. The branched peptides were synthesized starting from a Fmoc-Alanine-PEG-PS resin, with either one or two coupling cycles with Fmoc-K-Fmoc-OH activated with HATU/DIPEA. The following couplings were achieved using Fmoc amino acids activated with HATU/DIPEA. The Fmoc deprotection reagent was 1% DBU, 1% Piperidine in dimethylformamide. The peptides were cleaved from the resins by adding 10 ml of trifluoroacetic acid (TFA)/phenol/thioanisol/$H_2O$/ethandithiol 93/2/2/2/1 and incubated at room temperature for 5 hours. The mixtures were filtered and the peptides precipitated in cold ethyl ether. The precipitates were collected and solubilized in $H_2O$ for lyophilization. All peptides were purified by reverse phase high performance liquid chromatography (RP-HPLC), using a Dynamax RP C18 (300×10 mm i.d.), and equilibrated at 3 ml/min using a linear gradient from 5% $CH_3CN$ to 60% $CH_3CN$ in 0.1% TFA in 40 minutes. The fractions containing the peptide were acidified with 1 N HCl to help in the elimination of TFA, and lyophilized. Peptide identity was confirmed by time of flight matrix assisted laser desorption ionization mass spectroscopy. Purity was confirmed by analytical RP-HPLC.

For large-scale synthesis of N-acetyl-PGP, an alternative method was used to increase the yield of the product. In this method, the dipeptide t-Boc-PG was coupled to Pro-Merrifield resin using the dicyclohexylcarbodiimide/1-hydroxybenzotriazole procedure. After the removal of the N-terminal protection and acetylation using acetic anhydride, the peptide was cleaved from the resin using anhydrous hydrofluoric acid. The product was purified on a silica gel column using chloroform: methanol (90:10 v/v) as the eluent. Homogeneity was confirmed by RP-HPLC on a Vydac C18analytical column equilibrated at a flow rate of 1.2 ml/min an d eluted with a linear gradient from 0% to 30% acetonitrile in water (0.1% trifluoroacetic acid) in 30 minutes. Peptide identity was confirmed by Electrospray Mass Spectrometry (Perkin-Elmer-Sciex API-3). Quantitative amino acid analysis was performed to show the correct ratio of amino acids and to determine the peptide content for calculation of the final concentration.

EXAMPLE 4
Preparation of Solutions $LTB_4$ was dissolved in ethanol and diluted with HBSS (pH 7.3) to a final ethanol concentration of 0.001%. Synthetic complementary peptides and synthetic chemoattractants were dissolved in HBSS (pH 7.3). When necessary, the osmolality was adjusted between 280 and 320 mOsm by adding a small amount of distilled water.

EXAMPLE 5
Ultrafiltrate from Alkali-degraded Rabbit Corneas

Ultrafiltered tripeptide chemoattractants were obtained from alkali-degraded rabbit corneas. Corneal buttons were excised from rabbit eyes (Pel-Freez Biologicals, Rogers, Ariz.) using an 11 mm trephine. Based on an average dry weight of 11 mg/cornea in a preliminary experiment, corneas were placed in a known amount of 1.0 N NaOH (83.34 mg corneal dry weight/ml alkali, 1:12) for 24 hours at 37° C. The resultant suspension was titrated to pH 7.4 with 1.0 N HCl. This yielded a crude extract containing 41.67 mg corneal dry weight/ml of neutralized alkali. Briefly, the purification technique involved ultrafiltration (30,000, 3,000, and 1,000 Molecular Weight cutoff membranes in sequence) and dialysis (100 MWt cutoff membrane) of this crude extract.[4] The final ultrafiltrate was lyophilized and the powder dissolved in HBSS to a final concentration of 83.34 mg corneal dry weight/ml. This concentration was based on the original mg of corneal dry weight exposed to alkali.

According to a previous study[4], the ultrafiltered chemoattractant sample was composed of small peptides between 100 and 1,000 MWt. The only chemoattractants in this ultrafiltrate were N-acetyl-PGP and N-methyl-PGP. The specific activity of N-acetyl-PGP was found to be superior.

EXAMPLE 6
Neutrophil Isolation

These experiments followed the tenets of the Declaration of Helsinki and were approved by the human research committee a t Brookwood Medical Center. All donors signed written consent forms that explained the nature and possible consequences of the study. Blood was collected from only one donor each day.

Following the technique of Ferrante and Thong[13], polymorphonuclear leukocytes were isolated from fresh heparinized human whole blood by centrifugation on Hypaque-Ficoll (density=1.114) according to a described method[14]. Isolated polymorphonuclear leukocytes (96–99% viability) were resuspended in HBSS with 15 mM phosphate buffer at room temperature and gently agitated on a shaker. The purity of this cell suspension was $\geq$85% polymorphonuclear leukocytes, $\leq$5% mononuclear cells and platelets, with the remaining percentage consisting of red blood cells. Purified polymorphonuclear leukocytes were used in the polarization assay. All incubation mixtures were maintained between an osmolality of 280 to 320, a pH range of 7.2 to 7.6, 15 mM phosphate buffer, and 50 $\mu$M $Ca^{2+}$ and 50 $\mu$M $Mg^{2+}$.

EXAMPLE 7
Polarization Assay

Previous studies using the collagen gel-visual chemotactic assay[4] have shown N-acetyl-PGP to be a polymorphonuclear leukocyte chemoattractant. For chemotactic movement to occur the cell must take on a polarized morphology, therefore, polarization is a necessity for chemotaxis. When polarization is prevented by an inhibitor, chemotaxis is necessarily inhibited. For this experiment, it was therefore chosen to rely on the polarization results directly.

The polarization assay[15] was performed in a blind fashion. This assay was used to determine the polymorphonuclear leukocyte response to chemoattractants and inhibitors by measuring the frequency and degree of cellular shape change. Briefly, $2\times10^5$ polymorphonuclear leukocytes were mixed with preincubated synthetic complementary peptides and chemoattractants in a reaction chamber (total volume= 100 $\mu$l) at 37° C. for 5 min. At the end of the incubation period an aliquot was collected and mixed with an equal volume of 4% glutaraldehyde for microscopic observation. The remaining volume of each cell suspension was immediately centrifuged at 15,000× g for 5 seconds to remove cells. The resulting supernatant was analyzed for lactic dehydrogenase activity.[16] All incubations generated lactate dehydrogenase activity correlating with <5% cell death. Polymorphonuclear leukocytes in each sample were observed microscopically and assigned scores of 0 (resting= spherical cell with a smooth membrane), 1 (activated= irregular cell with uneven membranes) or 2 (polarized=cell length$\geq$width×2). Scores of 100 polymorphonuclear leukocytes for each sample were added to produce a polarization index. A dose response was performed for each chemoattractant. A concentration of each chemoattractant was chosen from the linear portion of each dose response curve and used as the positive control. Negative control samples consisted of polymorphonuclear leukocytes in HBSS only. Inhibition ($ID_{50}$) was expressed as the peptide concentration required to produce a 50% reduction in the polymorphonuclear leukocyte polarization response to the chemoattractant. The Student's t-test (unpaired) was used to analyze the differences in the mean polarization response between polymorphonuclear leukocytes activated with the chemoattractant in the absence or presence of complementary peptides.

EXAMPLE 8
D-RTR Tetramer Inhibition of N-acetyl-PGP or N-methyl-PGP Induced PMN Polarization The RTR complementary peptide has been shown to inhibit the polarization of polymorphonuclear leukocytes activated by N-acetyl-PGP. The complementary sequence, RTR, was designed to specifically interact hydropathically with the PGP sequence in N-acetyl-PGP and, therefore, should also interact with the same sequence in N-methyl-PGP. The D-RTR tetrameric peptide was designed to inhibit N-acetyl-PGP or N-methyl-PGP induced polymorphonuclear leukocyte polarization, but have a greater stability in vivo by resisting proteolytic degradation.

A preliminary study showed that the D-RTR tetramer inhibited (mean±SD) 800 $\mu$M N-acetyl-PGP induced polymorphonuclear leukocyte polarization as follows: 100 nM D-RTR tetramer=37%±35% inhibition (n=7), 1 $\mu$M D-RTR tetramer=65%±26% inhibition (n=6) and 10 $\mu$M D-RTR tetramer=92%±6% inhibition (n=6). The D-RTR tetramer inhibited (mean±SD) 1 mM N-methyl-PGP induced polymorphonuclear leukocyte polarization as follows: 1–10 $\mu$M D-RTR tetramer=14%±10% inhibition (n=5), 40–100 $\mu$M D-RTR tetramer=45%±7% inhibition (n=2) and 200–800 $\mu$M D-RTR tetramer=100% inhibition (n=5).

EXAMPLE 9
Results

All four complementary (antisense) peptides, containing the RTR sequence, showed substantial inhibition of N-acetyl-PGP activated polymorphonuclear leukocyte polarization (Table 1). The RTR tetrameric peptide was a powerful inhibitor of N-acetyl-PGP ($ID_{50}$ of 200 nM). The RTR dimer was much less potent ($ID_{50}$ of 105 $\mu$M). Both monomers, RTR ($ID_{50}$ of 2.5 mM) and RTRGG ($ID_{50}$ of 2.1 mM), were only antagonistic at millimolar concentrations. Preincubation of the RTR tetrameric peptide with N-acetyl-PGP or neutrophils for 5 min did not change the results described above. An additional antisense peptide, ASA tetramer, failed to show any inhibition of polymorphonuclear leukocytes activated by N-acetyl-PGP.

TABLE I

Complementary Peptide Inhibition of N-acetyl-PGP Activated PMN Polarization

| Complementary Peptides | Antagonist Activity ($ID_{50}$) | p-value |
|---|---|---|
| RTR tetramer | 200 nM ± 75 nM | <0.001 |
| RTR dimer | 105 $\mu$M ± 68 $\mu$M | 0.001 |
| RTR monomer | 2.5 mM ± 1.2 mM | <0.001 |
| RTRGG monomer | 2.1 mM ± 0.8 mM | <0.001 |
| ASA tetramer | None, $\leq$ 4 mM | — |

* Untreated PMNs (negative control) produced a polarization response of 7.8% ± 4.4% (n = 41).
PMNs activated with 500 $\mu$M N-acetyl-PGP (positive control) produced a polarization response of 56.5% ± 16.4% (n = 41).
This chemoattractant concentration was selected from the linear portion of the dose response curve, yielding approximately 50% polarization after subtraction of the negative control values.
Antagonistic activity ($ID_{50}$ mean ± standard deviation) was interpolated from five dose response curves for each complementary peptide.

The RTR tetramer and both monomeric peptides (RTR and RTRGG) also inhibited polymorphonuclear leukocytes activated b y the ultrafiltered tripeptide chemoattractants;

albeit at much higher concentrations (TABLE 2). None of the peptides were antagonistic to $LTB_4$ activation of polymorphonuclear leukocytes (TABLE 3). None of the complementary peptides stimulated resting polymorphonuclear leukocytes (TABLE 4).

TABLE 2

Complementary Peptide Inhibition of PMN Polarization Activated by Alkali-Degraded Rabbit Corneal Ultrafiltrate

| Complementary Peptides | Antagonist Activity ($ID_{50}$) | p-value |
|---|---|---|
| RTR tetramer | 30 µM ± 7 µM | <0.001 |
| RTR | 7.4 mM ± 1.6 mM | <0.001 |
| RTRGG | 9.0 mM ± 2.5 mM | <0.001 |

* Untreated polymorphonuclear leukocytes (negative control) produced a polarization response of 6.6% ± 1.4% (n = 10).
PMNs activated with the ultrafiltered tripeptide chemoattractants (25.0 mg original corneal dry weight degraded per ml of alkali) produced a positive control polarization response of 57.6% ± 4.4% (n = 10).
This chemoattractant concentration was selected from the linear portion of the dose response curve, yielding approximately 50% polarization after subtraction of the negative control values.
Antagonistic activity ($ID_{50}$, mean ± standard deviation) was interpolated from five dose response curves for each complementary peptide.

TABLE 3

Complementary Peptide Inhibition of $LTB_4$ Activated PMN Polarization

| Complementary Peptides | Antagonist Activity |
|---|---|
| RTR tetramer | None, ≦ 20 mM |
| RTR | None, ≦ 10 mM |
| RTRGG | None, ≦ 10 mM |

* Untreated polymorphonuclear leukocytes (negative control) produced a polarization response of 5.3% ± 2.1% (n = 6).
PMNs activated with $2 \times 10^{-9}$ M $LTB_4$ (positive control) produced a polarization response of 53.4% ± 11.3% (n = 6).
This chemoattractant concentration was selected from the linear portion of the dose response curve, yielding approximately 50% polarization after subtraction of the negative control values.
Antagonistic activity ($ID_{50}$, mean ± standard deviation) was determined from five dose response curves for each complementary peptide.

TABLE 4

Complementary Peptide Effects on Resting PMNs

| Complementary Peptides | Agonist Activity |
|---|---|
| RTR tetramer | None, ≦ 8 mM |
| RTR dimer | None, ≦ 8 mM |
| RTR | None, ≦ 40 mM |
| RTRGG | None, ≦ 40 mM |
| ASA tetramer | None, ≦ 16 mM |

* Untreated PMNs (negative control) produced a polarization response of 8.0% ± 3.2% (n = 8).
Agonistic activity was determined from five dose response curves for each complementary peptide.

EXAMPLE 10

Arginine-threonine-arginine Tetrameric Antisense Peptide Reduces Corneal Ulceration in the Alkali-injured Rabbit Eye Materials Sodium phosphate monobasic and sodium phosphate dibasic were obtained from Fisher Scientific (Fair Lawn, N.J.). Solvents for peptide synthesis were purchased from Fisher Scientific Products (West Chester, Pa.), while the reagents were from Perseptive Biosystem (Framingham, Mass.). Fmoc-d-Arg(Pbf)-OH and Fmoc-d-Thr(tBu)-OH were from Chem-Impex (Wood Dale, Ill.).

Peptide Synthesis

The RTR tetrameric peptide (($H_2$N-Arg-Thr-Arg-Gly-Gly)$_2$-Lys)$_2$-Lys-Ala-$CONH_2$), containing levorotatory (L) RTR sequences, was synthesized using Solid Phase Peptide synthesis following Fmoc methodology on a 9050 Peptide synthesizer from Perseptive Biosystem. This tetrameric peptide was synthesized starting from a Fmoc-Alanine-PEG-PS resin, with either one or two coupling cycles with Fmoc-K-Fmoc-OH activated with HATU/DIPEA. The following couplings were achieved using Fmoc amino acids activated with HATU/DIPEA. The Fmoc deprotection reagent was 1% DBU, 1% Piperidine in dimethylformamide. The peptide was cleaved from the resin by adding 10 ml of trifluoroacetic acid (TFA)/phenol/thioanisol/$H_2$O/ethanedithiol 93/2/2/2/1 and incubated at room temperature for 5 hours. The mixture was filtered and the peptide precipitated in cold ethyl ether. The precipitate was collected and solubilized in $H_2$O for lyophilization. The peptide was purified by reverse phase high performance liquid chromatography (RP-HPLC), using a Dynamax RP C18 (300×10 mm i.d.), and equilibrated at 3 ml/min using a linear gradient from 5% $CH_3$CN to 60% $CH_3$CN in 0.1% TFA in 40 minutes. The fractions containing the peptide were acidified with 1 N HCl to help in the elimination of TFA, and lyophilized. Peptide identity was confirmed by time of flight matrix assisted laser desorption ionization mass spectroscopy. Purity was confirmed by analytical RP-HPLC.

The RTR tetrameric peptide (($H_2$N-d-Arg-d-Thr-d-Arg-Gly-Gly)$_2$-Lys)$_2$-Lys-Ala-$CONH_2$), containing dextrorotatory (D) RTR sequences (only RTR was d conformation, the glycines and the polylysine core were not chiral), was synthesized manually starting with 3 g of the Fmoc-Pal-Peg-PS resin with an initial substitution of 0.2 mmol/g of resin. DMF was used as solvent for the coupling steps and the washing steps, while Fmoc deprotection was achieved with 1% DBU/2% Piperidine in DMF. Monitoring of the coupling and deprotection steps was conducted using the Kaiser test. All amino acids were doubly coupled for one hour, using as activating reagents, HOAt for the O-Pentafluorofenil ester amino acid and HATU/DIPEA for the free acids. An excess of 5 equivalents of amino acid over the resin substitution was used for alanine and the first lysine, 10 equivalents for the second lysine, and 20 equivalents for the following amino acids. The peptide was cleaved from the resins and purified as for the (L)-RTR peptide.

Preparation of Solutions

Synthetic peptides were dissolved in phosphate buffered saline (pH 7.3). The osmolality was between 280 and 320 mOsm.

Alkali-injury Model

Animals were maintained and treated in full compliance with the Association for Research in Vision and Ophthalmology (ARVO) Resolution on the Use of Animals in Research. Forty-eight New Zealand Dutch strain albino rabbits (Myrtles Rabbitry, Thompson Station, Tenn., U.S.A.) weighing 2.0 to 2.5 kg were anesthetized with ketamine HCl (12 mg/kg) and xylazine (7.5 mg/kg). Two drops of topical proparacaine (Allergan, Hormigueros, Puerto Rico) were placed in the right eye of each rabbit. Following ocular proptosis, a 12 mm plastic well was centered on the cornea and 0.4 ml of 1 N NaOH instilled into the well and left for a period of 35 sec. The alkali was aspirated and the well irrigated with 10 ml of physiological saline. Erythromycin ointment (0.5%) was applied two times a day and study medications given by the technique of Fraunfelder. Double blind examinations (slit lamp and dissecting microscopy) were conducted on Monday, Wednesday and Friday with photographs on Wednesday. Evaluation was made for the presence and size of epithelial defects, corneal ulceration, perforation and vascularization. Animals were randomly subdivided into two groups of 16 eyes each: 1) Phosphate buffered saline (PBS) control and 2) 800 µM (D)-RTR tetramer in PBS or 1.5 mM (L)-RTR tetramer in PBS alternating every hour. Each animal received one drop of the appropriate medication every hour for 14 hours a day for 33 days and dropping was discontinued until the end of the experiment on day 42.

Results

The clinical results at day 33 showed a statistically significant reduction in the frequency of corneal ulceration in the RTR tetramer group compared to the PBS group. There were 9 ulcers in the PBS group and 4 ulcers in the RTR tetramer group (p=0.0360).

The remaining days from day 33 to 42 transpired without any further topical dropping in any animal group. Despite cessation of all drops at day 33 the favorable effect of the RTR inhibitor (p=0.0046) persisted to the end of the experiment. The clinical results at day 42 are detailed in the table.

TABLE 5

| | RTR tetramer | PBS | Statistics (Chi-square) |
|---|---|---|---|
| NUMBER OF EYES | 16 | 16 | |
| ULCER DEPTH | | | |
| No Ulcer | 9 | 2 | |
| Anterior | 4 | 6 | |
| Middle | 0 | 3 | |
| Posterior | 2 | 4 | |
| Descemetocele | 1 | 1 | |
| Perforation | 0 | 0 | |
| TOTAL ULCERS | | | |
| During expt | 7 (43.8%) | 14 (87.5%) | p = 0.0046, very significant (RTR vs PBS) |
| End of expt (day 42) | 6 (37.5%) | 12 (75%) | p = 0.0163, significant (RTR vs PBS) |

Discussion

Alkali-injury to the eye degrades many proteins in all layers of the cornea by hydrolysis of peptide bonds and destruction of certain amino acids.[17] This degradation of cellular and extracellular corneal proteins directly releases two neutrophilic tripeptide chemoattractants.[5] Subsequent in vitro experiments identified these chemoattractants as N-acetyl-PGP and N-methyl-PGP and confirmed their chemotactic properties.[4] The acetylated tripeptide was the one more active. Intrastromal injection of synthetic N-acetyl-PGP or the ultrafiltered tripeptide chemoattractants into normal cornea demonstrated heavy neutrophil invasion to the injection site.[6] Taken together these findings substantiated the role of this tripeptide chemoattractant in triggering the early neutrophil response in the alkali-injured eye, confirming its importance as an inflammatory mediator.

Using the molecular recognition theory, RTR complementary peptides were designed and synthesized that were found to be inhibitors of N-acetyl-PGP. The capacity of these complementary peptides to inhibit polymorphonuclear leukocyte polarization varied with the chemoattractant. The most potent complementary peptide, RTR tetramer, showed greater inhibitory potency for synthetic N-acetyl-PGP compared to the ultrafiltered tripeptide chemoattractants. This might be the result of non-specific interaction with the heterogeneous group of small peptides (100–1,000 MWt) known to be present in the latter sample. The additional fact that these complementary peptides did not inhibit $LTB_4$ activated polarization demonstrates that they are not directly acting on the neutrophil in a non-specific manner. The absence of $LTB_4$ inhibition and the scarcity of extracellular LDH release from all incubations confirms that RTR complementary peptides were not toxic to neutrophils. Finally, these results also indicate that N-acetyl-PGP binds to a different neutrophil receptor than $LTB_4$.

The molecular recognition theory (or complementary peptides) posits that the pattern of hydropathy of amino acids is a gross determinant of shape and rudimentary function of that peptide or protein.[7] Therefore, inverting this hydropathic pattern should result in a peptide with a complementary shape, since the same driving forces are involved, but in reverse orientation. Hence it is given the name complementary peptides. Such complementary peptides have been shown to specifically interact with their targets with moderate affinity.[18] One way to achieve this inversion of hydropathy relies on an interesting characteristic of the genetic code. That is, since A and U are complementary, and when in the middle base of the codon specifies hydrophilic and hydrophobic respectively, then the non-coding strand of DNA (or mRNA) will code for a peptide which is complementary to the peptide encoded by the coding strand. Apart from being a useful method for designing complementary peptides, this suggests a mechanism for the evolution of interacting ligand pairs. However, using this DNA-based design method does not always result in the optimal pattern of hydropathic complementarity. For this reason it has also proved useful to design complementary peptides based on the hydropathic pattern of the target peptide using computer programs.[19]

The concept of complementary peptides based on hydropathic patterns was first tested with the peptide hormone corticotropin (ACTH). A complementary peptide HTCA, was synthesized corresponding to the noncoding strand of ACTH mRNA and tested for its ability to bind to ACTH. In a solid-phase binding assay, ACTH was found to specifically bind to this complementary peptide, HTCA, with nanomolar affinity.[20] Further, equivalent binding was observed with HTCA peptides based on a sense or antisense reading of ACTH complementary RNA.[21] The observation that these peptides had different amino acid sequences but the same linear array of hydropathy suggested that this latter property was responsible for the interaction. Additional support for the idea that inverted hydropathy is the driving force for the interaction comes from the observation that complementary peptides interact when derived from computer-assisted inversion or nucleotide sequence-directed inversion.[22]

Complementary peptides derived from molecular recognition theory have been used in a wide variety of systems as antagonists.[23-26] The present invention described the design of complementary peptides that specifically bind and alter the activity of the chemotactic ligand, N-acetyl-PGP. Since the hydropathic characteristics of proline are not very well defined, two complementary peptides to the N-acetyl-PGP were designed. One peptide, ASA, was based on the Kyte and Doolittle scale[11] and the other peptide, RTR, was based on the Akamatsu and Fujita scale[12]. The latter is based upon the partition coefficients of di- and tri-peptides, making it more appropriate for the design of a complementary peptide to such a small target. The complementary peptides were also synthesized and tested as tetramers, a common approach used to enhance binding affinity for the target.[27,28] Multimerization increases the stoichiometry of the reaction, sequestering a greater number of chemoattractant molecules, hence reducing the dose of the complementary peptide necessary to block N-acetyl-PGP.

The inhibitory properties of the RTR complementary peptides are predicated on the molecular interaction of the RTR sequence with N-acetyl-PGP. This fact is made clear by comparing the $ID_{50}$ values for each complementary peptide against N-acetyl-PGP. The inhibitory properties of both monomeric peptides, RTR and RTRGG ($ID_{50}$=2 mM), were 20-fold less than the RTR dimer which was 500-fold less than the RTR tetramer. The ASA complementary peptide (with a polylysine core and di-glycine spacer identical to the RTR tetramer) serves as a control for the tetramer core and as a control for the RTR sequence. The absence of inhibitory activity from the ASA tetramer proves that the polylysine core and another hydropathic tripeptide sequence is not active. These results show that the RTR peptide is specific for N-acetyl-PGP, given that the ASA sequence fails to block N-acetyl-PGP activation of polymorphonuclear leukocyte polarization.

The affinity of the RTR tetrameric peptide for N-acetyl-PGP was 10,000-fold greater than the RTR monomer. It is possible that the high charge distribution on the multimeric peptide, resulting from the arginine side chains, reduces the number of RTR conformations in the tetramer as compared to the RTR monomer. The presence of favorable binding conformers in this limited number of conformations would increase the binding affinity with the chemoattractant. Alternately, or in addition, the close association of the RTR branches in the tetamer might limit the diffusion parameters of N-acetyl-PGP, keeping the chemoattractant in closer association with the tetramer and changing the kinetics of the interaction. These findings are consistent with an increasing effect as the multimeric structure increases the number of RTR sequences.

Peptides comprised of L-amino acids are rapidly degraded by enzymes in the body, especially in inflamed tissues. The D-form of complementary peptides has been shown to retain the biological activity of the L-form,[18,19,29] yet is more resistant to proteases and therefor more stable in vivo. For this reason the RTR tetramer, D-forms of all amino acids, may be an alternative therapeutic agent.

The implications of the methods of the present invention for the treatment of patients with alkali-injury of the eye might b e substantial. If an inhibitor of polymorphonuclear leukocyte chemotaxis is administered immediately after an injury, the stimulus for polymorphonuclear leukocyte invasion into the cornea might be abrogated. Neutrophils constitute one of the most serious dangers to corneal integrity by initiating and perpetuating ulceration and causing perforation of the eye. If the initial recruitment of polymorphonuclear leukocytes by N-acetyl-PGP can be abolished or diminished, then other mediators, that are released from polymorphonuclear leukocytes, would not have an opportunity to magnify this neutrophilic response. The end result is preservation of the corneal stroma, maintaining globe integrity and providing a suitable substratum upon which epithelial regrowth is encouraged.

Discovery of the alkali-generated chemoattractant has lead to a fuller understanding of chemotaxis in alkali-injuries and might also give rise to useful treatment in other eye diseases and in inflammation in other tissues of the body. For example, when soft tissue is injured by alkali anywhere in the body presumably the same chemoattractant is generated which would participate in triggering the inflammatory cycle initiated by alkali in these tissues. An example of this was observed with a variety of human blood components which elicited a polymorphonuclear leukocyte polarization response after exposure to alkali. It is conceivable that this genre of inhibitors might act to blunt the polymorphonuclear leukocyte inflammatory response in other unrelated, non-traumatic diseases where the chemoattractant is the same or sufficiently similar.

The use of this new methodology substantially shortens the time course for development of lead compounds; reducing the iterative approach in both traditional and computer molecular modeling techniques. This antisense technology might hold a key to the treatment of other diseases where mediators are known or can be identified. The practical implications of this research are far reaching, including the development of high potency compounds which might be beneficial to alkali-injured eyes or other types of diseases.

The in vitro experiments have conclusively shown that the (D) and (L) RTR tetramer was highly inhibitory to the neutrophil chemoattractants released in the early stages in the alkali-injured eye. When this tetramer was applied to the alkali-injured rabbit eye a statistically significant decrease in corneal ulceration was identified when compared to the control group. The affinity of the RTR tetramer for the chemoattractants appearing after alkali-injury defeat their polymorphonuclear leukocyte chemotactic properties immediately and thereby reduce ulceration in the short and long term. Proof for this latter statement is found in the continuing protective effect past day 33 when all medication had been stopped.

N-acetyl-PGP and N-methyl-PGP are the primary neutrophil chemoattractants released into the stroma by direct hydrolysis of corneal proteins immediately after an alkali-injury. These chemoattractants are thought to trigger the subsequent heavy infiltration of neutrophils that leads to corneal ulceration. It is likely that the complementary binding of RTR tetramer to N-acetyl-PGP and N-methyl-PGP, shortly after the injury, inactivated these chemoattractants in the cornea, reducing the early and then subsequent neutrophilic invasion. Exclusion of polymorphonuclear leukocytes protects the injured corneal tissue from the degradative enzymes and oxygen free radicals contained in these inflammatory cells. These considerations explain the persistent therapeutic effect of RTR treatment and suggest that early treatment of the alkali-injured eye, for a shorter interval, might yield a similar result.

This experiment demonstrates that (D) and (L)-RTR tetramer, used alternately in the same eye, significantly reduced the incidence of corneal ulcers occurring after alkali-injury. The potential for enzymatic degradation of peptides at different stages of healing in an alkali-injured cornea is unknown. A paucity of corneal cells in the first few days after the injury would be consistent with low enzymatic activity in this time period. Other studies report that (D)-antisense peptides have similar biologic activity to (L)-peptides and that (D)-peptides are stable in vivo.[18,19,29] Corneal enzymes might be capable of degrading the (L)-RTR tetramer. The rationale for administering both tetramers on alternate hours to the same eye was to prevent enzymatic degradation of a portion of the tetramer, keeping the total RTR tetramer concentration higher.

The following references were cited herein:
1. Brown, et al., Otolaryngol. 1970; 74:375–383.
2. Kenyon, et al., Invest Ophthalmol Vis Sci. 1979;18:570–587.
3. Foster, et al., Arch Ophthalmol. 1982;100:1820–1824.
4. Pfister, et al., Invest Ophthalmol Vis Sci. 1995;36:1306–1316.
5. Pfister, et al., Invest Ophthalmol Vis Sci. 1996;37:230–237.

6. Pfister, et al., Invest Ophthalmol Vis Sci. 1998;39:
7. Blalock, Nature Medicine. 1995;1:876–878.
8. Blalock, et al., Biochem Biophys Res Commun 1–984; 1–21:203–207.
9. Blalock, et al., Trends Biotechnol 1990; 8:140–144.
10. Clarke, et al., In: Antisense Nucleic Acids and Proteins: Fundamentals and Applications vandrol Krol AV and Mol JNM (eds): Dekker, New York: 169–186 (1991).
11. Kyte, et al., J Mol Biol 1982;157:105–132.
12. Akamatsu, et al., Journal of Pharmaceutical Science 1992;2:164–174.
13. Ferrante, et al., J Immunol Methods 1978;24:389.
14. Pfister, et al., Cornea. 1984/1985;3:183–188.
15. Haston, et al., J Immunol Methods. 1985;81:229–237.
16. Decker, In Worthington Enzyme Manual. Freehold, N.J., Worthington Biochemical Corp., 1977, p19-22.
17. Berry, et al., Cornea 1989;8:150–154.
18. Fassina, et al., Arch Biochem Biophys 1992;296:137–143.
19. Fassina, et al., Int J Peptide Protein Res 1992;39:540–548.
20. Bost, et al., Proc Natl Acad Sci USA 1985;82:1372–1375.
21. Blalock, et al., Biochem J 1986;234:679–683.
22. Fassina, et al., J Biol Chem 1989;264:11252–11257.
23. Budisavljevic, et al., J Hypertension 1992;19:345–353.
24. Gartner, et al., Proc Soc Exp Biol Med 1991–198:649–655.
25. Gartner, et al., Biochem Biophys Res Commun 1991;180:1446–1452.
26. Johnson, et al., J Immunol 1988;141:2420–2423.
27. Fassina, et al., Int J Peptide Protein Res 1992;39:549–556.
28. Tam, Proc Natl Acad Sci USA 1988; 85:5409–5413.
29. Fassina, et al., J Biol Chem 1989;264:11252–11257.

Any patents or publications mentioned in this specification are indicative of the levels of those skilled in the art to which the invention pertains. Further, these patents and publications are incorporated by reference herein to the same extent as if each individual publication was specifically and individually indicated to be incorporated by reference.

One skilled in the art will appreciate readily that the present invention is well adapted to carry out the objects and obtain the ends and advantages mentioned, as well as those objects, ends and advantages inherent herein. The present examples, along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A pharmaceutical composition for ophthalmologic uses, comprising a complementary peptide having a sequence complementary to prolineglycine-proline (PGP) (SEQ ID NO:1), wherein said complementary peptide is selected from the group consisting of RTR (SEQ ID NO:2), RTRGG (SEQ ID NO:3), RTR dimer, RTR tetramer, RTR octamer, N-acetyl-RTR multimer, short-chain and long-chain fatty acid RTR multimer, RTR multimer using diaminopropionic acid for the core subunit, RTR multimer using diaminobutyric acid for the core subunit, RTR multimer containing a spacer having the formula $NH_2[CH_2]_n$—COOH[n=2[3-aininopropionic acid];3;4;5;6; or 7[8-aminocaprylic acid]], said spacer replacing diglycine spacer, cysteine RTR multimer having a bicyclic structure, and XTR multimer with N-terminal modifications and core subunit modifications, wherein said complementary peptides have dextrorotatory amino acids substituting for the natural levorotatoxy, and wherein X may be any amino acid.

2. A method of inhibiting polymorphonuclear leukocyte polarization, chemotaxis, and infiltration into tissue activated by a neutrophil chemoattractant in an individual, comprising the step of administering to said individual a pharmaceutical composition for ophthalmologic uses, so as to inhibit polymorphonuclear leukocyte infiltration into tissue, wherein said neutrophfl chemoattractant is selected from the group consisting of N-acetyl-PGP, N-acetyl-PGX, N-methyl-PGX, N-methyl-PGP, and small peptide chemoattractants containing proline and glycine, wherein said pharmaceutical composition comprises a complementary peptide having a sequence complementary to proline-glycine-proline (PGP) (SEQ ID NO:1), and wherein X may be any amino add.

* * * * *